United States Patent [19]

Van Himbergen et al.

[11] Patent Number: 5,762,844

[45] Date of Patent: Jun. 9, 1998

[54] SIDE-BY-SIDE ABSORBENT PAD FORMING

[75] Inventors: James George Van Himbergen, Kimberly; Thomas George Olsen, Neenah, both of Wis.; James Joseph Wiltzius, Ogden, Utah; John Wallace de Vos, Appleton, Wis.; Leon Robert Flesburg, Neenah, Wis.; Ryan Joseph Roth, Kimberly, Wis.; Brian Keith Costelic, Greenville, Wis.

[73] Assignee: Kimberly-Clark Worldwide, Inc., Neenah, Wis.

[21] Appl. No.: 834,394

[22] Filed: Apr. 16, 1997

Related U.S. Application Data

[60] Provisional application No. 60/027,431, Dec. 5, 1996.

[51] Int. Cl.$^6$ .................................. B27N 3/04; A61F 13/15
[52] U.S. Cl. .................... 264/112; 264/517; 264/113; 264/116; 425/80.1; 425/81.1; 425/82.1
[58] Field of Search ......................... 264/517, 112, 264/113, 116; 425/80.1, 81.1, 82.1

[56] References Cited

U.S. PATENT DOCUMENTS

| | | | |
|---|---|---|---|
| 4,666,647 | 5/1987 | Enloe et al. | 264/121 |
| 4,761,258 | 8/1988 | Enloe et al. | 264/518 |
| 4,767,586 | 8/1988 | Radwanski et al. | 264/113 |
| 4,904,440 | 2/1990 | Angstadt | 264/517 |
| 4,921,659 | 5/1990 | Marshall et al. | 264/510 |
| 5,004,579 | 4/1991 | Wislinski et al. | 264/517 |
| 5,093,963 | 3/1992 | Farrington et al. | 19/296 |
| 5,591,148 | 1/1997 | McFall et al. | 604/378 |

*Primary Examiner*—Mary Lynn Theisen
*Attorney, Agent, or Firm*—Paul Yee

[57] ABSTRACT

A distinctive method and apparatus (20) for forming a composite fibrous web (22) includes a web supply (24, 25), which provides at least two appointed fiber layer sections (26, 28) of desired fiber material. Each of the layer sections (26, 28) has a selected composition. A fiberizer (30) disintegrates each of the fiber layer sections (26, 28) into individual, laterally adjacent fiber streams (32, 33) while substantially maintaining a lateral separation of the fiber streams while the fiber streams (32, 33) are moving through the fiberizer (30). A directing channel (34) delivers the fiber streams (32, 33) from the fiberizer (30) to a forming chamber (40). The forming chamber (40) is configured to substantially maintain the separation of the fiber streams. A foraminous forming surface (48) is disposed within the forming chamber (40), and is configured to receive each of the fiber streams (32, 33) to produce individual, fibrous web sections (76a, 76b) substantially corresponding to the individual fiber streams (32, 33). A transporter (60) removes the fibrous web sections (76a, 76b) from the forming surface (48), and an integrator (62) laterally displaces and superposes one of the fibrous sections (32, 33) onto another of the fibrous web sections to provide the composite fibrous web (22).

22 Claims, 10 Drawing Sheets

SIDE-BY-SIDE ABSORBENT PAD FORMING

This application claims priority from U.S. provisional application Ser. No. 60/027,431, filed on Dec. 5, 1996.

FIELD OF THE INVENTION

The present invention relates to a method and apparatus for forming a fibrous web. More particularly, the present invention relates to a method and apparatus for forming discrete fibrous web sections on laterally adjacent regions of a forming surface.

BACKGROUND OF THE INVENTION

Conventional techniques have employed a foraminous forming belt or a foraminous forming surface of a rotating forming drum to produce fibrous webs having selected contours and selected peripheral shapes. In particular, such techniques have been employed to form airlaid fibrous webs composed of cellulose wood pulp fluff.

Conventional techniques have also been configured with multiple forming drums arranged in-line, in series with each other to provide a composite fibrous web having multiple layers stacked on top of each other. Other conventional techniques have been employed to incorporate selected amounts of superabsorbent material into selected regions of a fibrous web layer.

Conventional techniques, such as those described above, have been complicated and have required the use of multiple forming devices, such as multiple forming drums. The cost of using the multiple forming devices has been excessive, and the techniques employing the multiple forming devices have required excessive amounts of space. As a result, there has been a continued need for lower cost, space-efficient methods and apparatus for forming composite fibrous webs composed of multiple fibrous layers.

BRIEF DESCRIPTION OF THE INVENTION

Generally stated, an apparatus for forming a composite fibrous web includes a web supply which provides at least two appointed fiber layer sections of fiber material, each of the layer sections having a selected composition. A rotatable fiberizer disintegrates each of the fiber layer sections into individual, laterally adjacent fiber streams having the selected compositions. The fiberizer is configured to disintegrate the fiber layer sections while substantially maintaining a lateral separation of the fiber streams while the fiber streams are moving through the fiberizer. A directing channel delivers the fiber streams from the fiberizer to a forming chamber, and the forming chamber is configured to substantially maintain the separation of the fiber streams. A foraminous forming surface is disposed within the forming chamber, and is configured to receive each of the fiber streams to produce individual, fibrous web sections substantially corresponding to the individual fiber streams. A transporter removes the fibrous web sections from the forming surface, and an integrator laterally displaces at least one of the fibrous web sections to superpose the one of the fibrous web sections onto another of the fibrous web sections to provide the composite fibrous web.

In a process aspect of the invention, a method for forming a composite fibrous web includes a lateral displacing of at least one fibrous web section to superpose a first fibrous web section onto a second fibrous web section to form the composite fibrous web. The first and second fibrous web sections have been provided by a supplying of at least two appointed, fiber layer sections of fiber material, each of the layer sections having a selected composition. The fiber layer sections have been disintegrated into individual, laterally adjacent fiber streams. The disintegration of the fiber layer sections have been conducted while substantially maintaining a lateral separation of the fiber streams while moving the fiber streams through the disintegration operation. The fiber streams have been delivered to a forming chamber while substantially maintaining the lateral separation of the fiber streams. The fiber streams have been received onto a foraminous forming surface within the forming chamber to produce individual, fibrous web sections substantially corresponding to the individual fiber streams, and the fibrous web sections have been removed from the forming surface.

The various aspects of the invention can advantageously provide a method and apparatus which can be less expensive, and more space efficient. The various aspects of the invention can also reduce the need for selectively cutting and placing fibrous web components into desired locations along a moving substrate web, and can reduce problems which are related to controlling the desired registration between the moving substrate and the assembled fibrous web components. In its various aspects, the invention can provide a composite fibrous web having individual, discrete layers wherein each layer has been configured with a desired composition, size, and/or shape.

BRIEF DESCRIPTION OF THE DRAWINGS

The present invention will be more fully understood and further advantages will become apparent when reference is made to the following detailed description of the invention and the drawings, in which:

FIG. 4A representatively shows an end view of the forming surface segment illustrated in FIG. 4;

FIG. 4B representatively shows a cross-sectional view taken along line B—B of the forming surface segment illustrated in FIG. 4;

FIG. 7A representatively shows a schematic, enlarged cross-sectional view of a portion of a scarfing roll having repositionable scarfing pins;

DETAILED DESCRIPTION OF THE INVENTION

Figure 1:
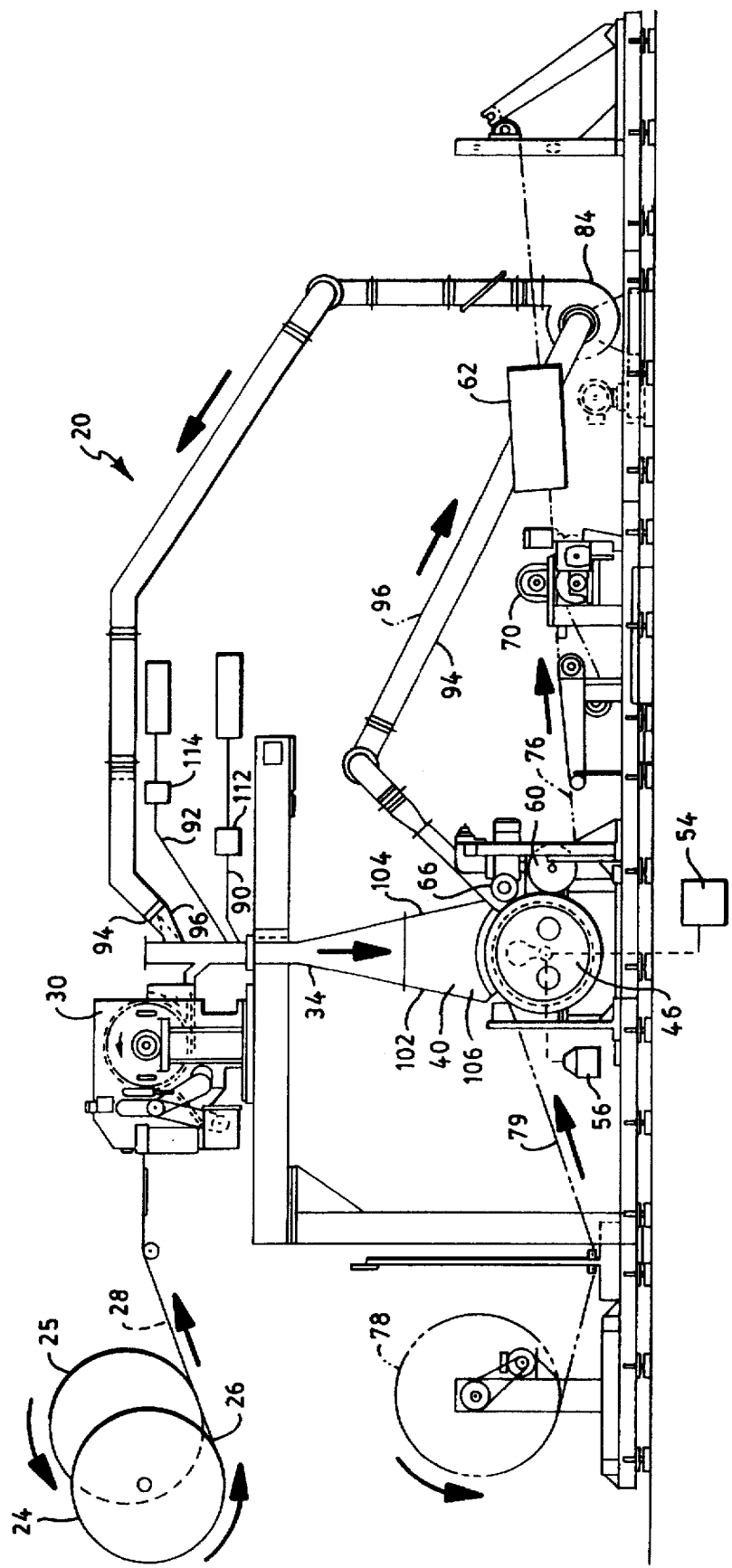
FIG. 1 representatively shows a schematic, side view of the method and apparatus of the invention.
Figure 1A:
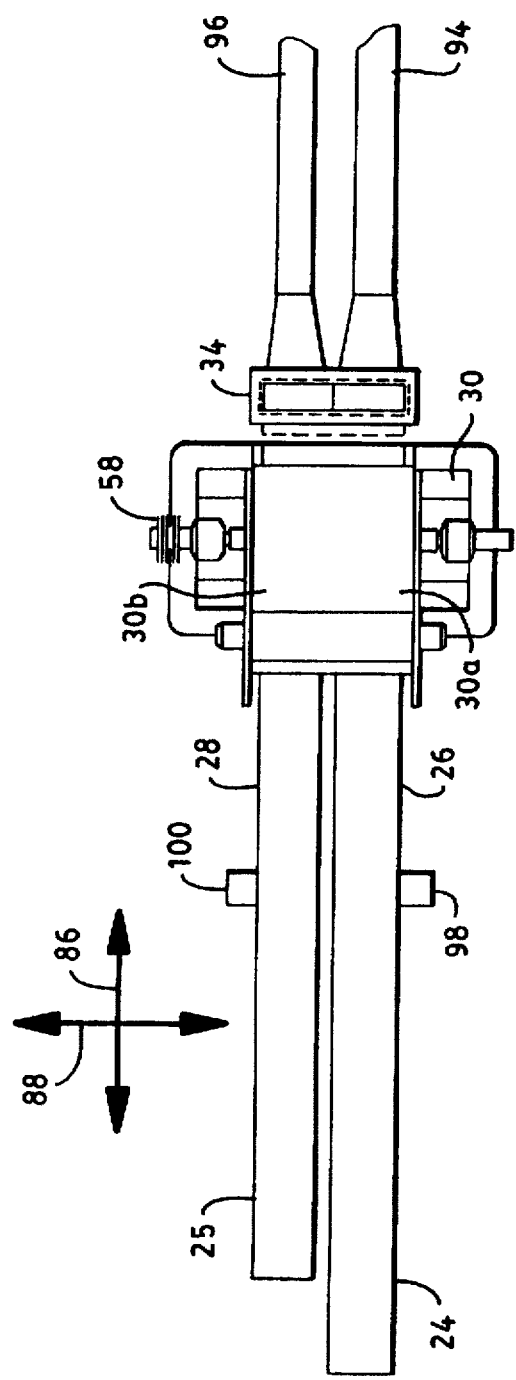
FIG. 1A representatively shows a schematic top view of a fiberizer system employed with the method and apparatus of the invention.

With reference to FIGS. 1 and 1A, the representatively shown method and apparatus 20 for forming a composite fibrous web 22 includes a web supply, such as provided by web supply rolls 24 and 25, which provides at least two appointed fiber layer sections 26 and 28 of desired fiber material. Each of the layer sections 26 and 28 has a selected composition. A fiberizer 30 disintegrates each of the fiber layer sections 26 and 28 into individual, laterally adjacent fiber streams 32 and 33 while substantially maintaining a lateral separation of the fiber streams while the fiber streams 32 and 33 are moving through the fiberizer 30. A directing channel 34 delivers the fiber streams 32 and 33 from the fiberizer 30 to a forming chamber 40. The forming chamber 40 is configured to substantially maintain the separation of the fiber streams. A foraminous forming surface 48 is disposed within the forming chamber 40, and is configured to receive each of the fiber streams 32 and 33 to produce a formed fibrous web 76. The formed web 76 has individual, fibrous web sections 76a and 76b (FIG. 5) which substantially correspond to the individual fiber streams 32 and 33. A transporter 60 removes the fibrous web sections 76a and 76b from the forming surface 48, and an integrator 62 laterally displaces at least a one of the fibrous sections 32 or 33 to superpose the one of the fibrous web sections onto another of the fibrous web sections to provide the composite fibrous web 22. In the illustrated configuration, for example, the first fibrous web section 76a is displaced or superpositioned onto the second fibrous web section 76b.

The representatively shown method and apparatus 20 have a generally length-wise extending, machine-direction 86, and a laterally extending, cross-direction 88. For the purposes of the present description, the machine-direction 86 at any particular local region of the method and apparatus will be the direction along which the selected component or work material is being directed through the process equipment at that particular location. The cross-direction 88 at the particular local region along the process and apparatus is substantially perpendicular to the local machine-direction 86, and lies substantially within the general plane of the appointed component or work material being directed through the process or apparatus.

The web supply mechanism can employ any conventional technique for delivering desired quantities of fibrous material. The fibrous material may be provided in the form of bales, separated sheets, rolled sheets, or the like, as well as combinations thereof. In the illustrated configuration, for example, the supplying mechanism includes a pair of web supply rolls 24 and 25. Optionally, the web supply mechanism may include a single supply roll for providing a single layer of fiber material which can be cut or otherwise separated to provide the at least two appointed fiber layer sections 26 and 28. In the illustrated embodiment, the first web supply roll 24 provides the first fiber layer section 26, and the second web supply roll 25 provides the second fiber layer section 28. With reference to FIG. 1A, the web layer supply system can be configured to provide the fiber layer sections 26 and 28 in a substantially side-by-side, laterally adjacent relation.

Each of the fiber layer sections has a selected composition. In a particular arrangement of the invention, each of the fiber layer sections 26 and 28 can have substantially the same composition. Alternatively, each of the fiber layer sections can have a different composition of fibers. For example, the first fiber layer section 26 can have a composition which includes a natural wood pulp fiber, such as Coosa 1654 wood pulp, a high bulk wood pulp fiber, such as Buckeye HPF wood pulp, a stiff wood pulp fiber, such as Eucalyptus wood pulp, or a binder type fiber, such as Hoechst Celanese Celbond T105/T255. In addition, the composition of the fiber layer section 26 may be any desired combination of these materials.

The second fiber layer section 28 can have any of the compositions employed for the fiber layer section 26, and composition of the second fiber layer section may be the same as or different than that of the first fiber layer section. For example, when compared to the first fiber layer section 26, the second fiber layer section 28 may have a composition which is substantially identical, a composition having a combination of similar of fibers with a different mix ratio, or a totally different composition.

In other aspects of the invention, the first and second fiber layer sections 26 and 28 may have the same density and/or basis weight. Alternatively the fiber layer sections may have different densities and/or different basis weights to provide improved benefits.

Particular aspects of the invention can include a web supply mechanism which incorporates a regulator to control the speed, the mass and/or the volume of fiber material being delivered from each of the web supply rolls 24 and 25. For example, the web supply roll 24 may include a first feed regulator 98, and the second web supply roll 25 can include a second feed regulator 100. The desired composition and characteristics of the formed fibrous web sections 76a and 76b can, for example, be appropriately controlled by adjusting the compositions of the first fiber layer 26 and the second fiber layer 28, and by adjusting the feed regulators 98 and 100 to modify the rates at which the individual fiber layer sections 26 and 28 are introduced into the fiberizer 30.

The fiberizer 30 can be any mechanism which operably disintegrates each of the fiber layer sections 26 and 28 into the desired, laterally adjacent fiber streams 32 and 33. In a particular aspect of the invention, the fiberizer 30 was configured to disintegrate the fiber layer section 26 and 28 while substantially maintaining an operative lateral separation or other segregation of the streams of disintegrated fibrous material while the streams of fibrous material are moving through the fiberizer 30. In further aspects of the invention, the fiberizer can operably provide individual, laterally adjacent fiber streams 32 and 33 having individual compositions which correspond to the selected compositions provided by the first and second fiber layer sections 26 and 28, respectively.

Other aspects of the invention can include a fiberizer 30 which is configured to provide the fiber streams 32 and 33 with not more than about 5 percent (%) lateral mixing between fiber streams, as determined with respect to a total basis weight of an individual fibrous web section 76a or 76b. Alternatively, there can be not more than about 10 percent lateral mixing between the fiber streams, and optionally can be not more than about 20 percent lateral mixing between the fiber streams, as determined with respect to a total basis weight of an individual fibrous web section to provide desired levels of performance.

In addition to the particular configuration of the fiberizer 30, the amount of lateral mixing between the fiber streams in the fiberizer can, for example, be controlled by adjusting the lateral spacing distance between the fiber layer sections 26 and 28 where the fiber layer sections are introduced and fed into the fiberizer. In particular aspects of the invention, the lateral spacing distance between the fiber layer sections can be at least about 1 inches (about 2.54 cm). Alternatively the lateral spacing distance can be at least about 3 inches (about 7.6 cm), and alternatively can be at least about 5 inches (about 12.7 cm), or more, to provide desire levels of segregation between the fiber streams in the fiberizer.

In the method and apparatus of the invention, the fiberizer 30 can be configured to provide the fiber streams 32 and 33 with one or more passes of each of the fiber layer sections of fiber material through the fiberizer. In particular aspects of the invention, the fiberizer 30 is configured to provide each of the fiber streams 32 and 33 with only a single pass of the disintegrated fiber material through the fiberizer. Accordingly, the material of fiber layer section 26 passes through its appointed portion of the fiberizer a single time, and the fibrous material from the fiber layer section 28 also passes through its appointed portion of the fiberizer a single time. With such an arrangement, the fiberizer 30 is desirably a screenless-type of fiberizer, and is configured to substantially avoid recirculating the fiber material from the fiber layer sections 26 and 28 back through the fiberizer with additional transit paths through the disintegration operation.

The fiberizer mechanism 30 includes an operative drive system 58, such as provided by an internal combustion engine, an external combustion engine, an electromechanical, and electro-magnetic motor, a line-shaft driving system, or the like, as well as combinations thereof. The drive system 58 can be any conventional driving technique which includes sufficient power to rotate or otherwise operate the fiberizer at a sufficient speed and throughput rate.

Figure 3A:
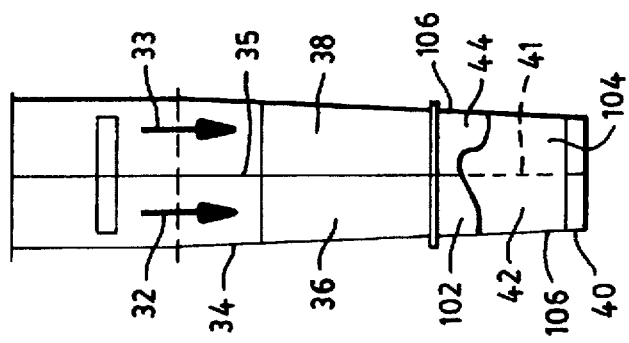
FIG. 3A representatively shows a schematic, partially cut away, end view of the directing channel and forming chamber of the invention.
Figure 3:
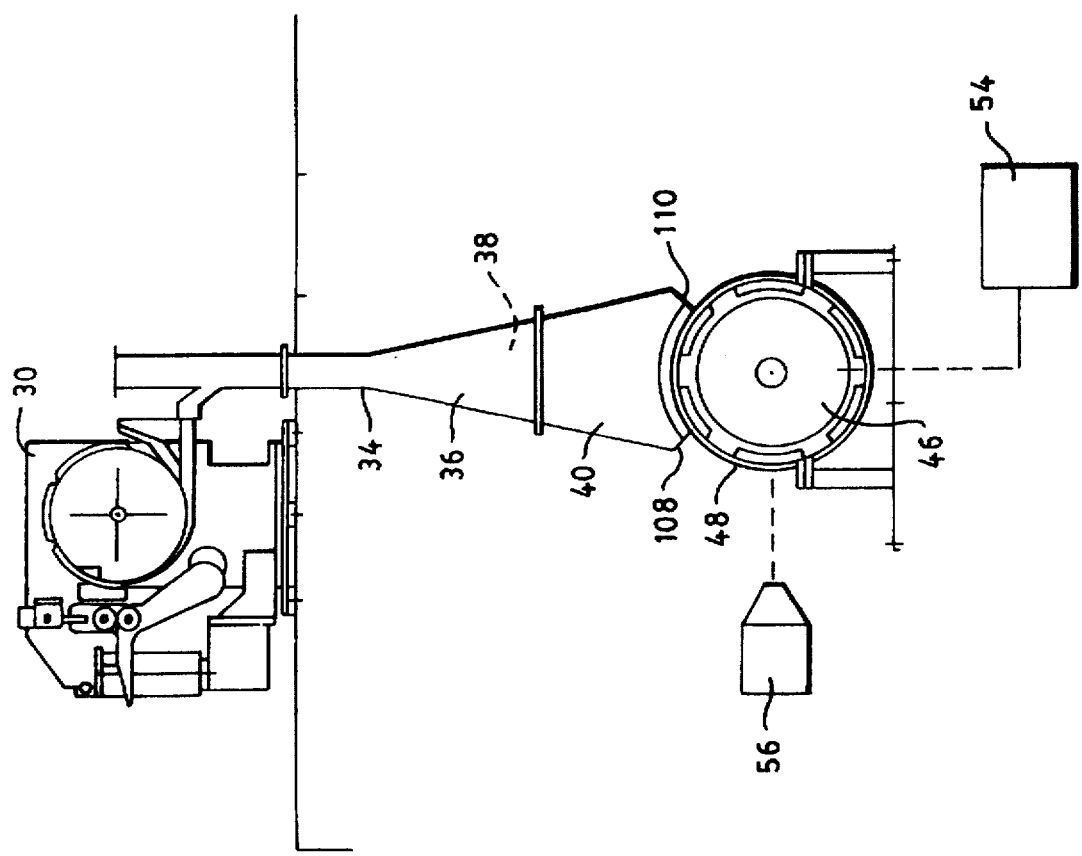
FIG. 3 representatively shows a schematic, side view of the directing channel and forming chamber of the invention.

In desired aspects of the invention, the first fiber layer section 26 is delivered into a first fiberizer section 30a, and the second fiber layer section 28 is delivered into a second fiberizer section 30b, as representatively shown in FIG. 1A. The fiberizer is desirably configured to simultaneously disintegrate each of the fiber layer sections to provide individual, discrete fiber streams 32 and 33 (e.g. FIG. 3A), respectively, which are positioned laterally adjacent to each other. Each of the fiber streams 32 and 33 can have an individual composition which substantially corresponds to the composition of the material forming its associated fiber layer section 26 and 28, respectively.

In the example of the shown configuration, the fiberizer sections 30a and 30b are laterally-coupled, and there is a substantially direct coupling between the fiberizer sections. Optionally, there may be an indirect coupling between the fiberizer sections, and the type of direct or indirect coupling may mechanical, electromechanical, electromagnetic, electronic or the like, as well as combinations thereof.

To substantially maintain the desired lateral separation of the fiber streams 32 and 33 while the fiber streams are moving through the fiberizer, the fiberizer 30 can include a suitable system of internal baffles. In particular aspects of the invention, the desired lateral separation of the fiber streams 32 and 33 within the fiberizer 30 can be operatively provided without employing internal baffles positioned between the fiber streams within the fiberizer. For example, the fiberizer 30 can have the configuration of a "CET" (constant energy transmission) fiberizer, such as a screenless rotor mill in a model with horizontal discharge, available from JOA, a company having offices in Sheboygan Falls, Wis. Alternatively the fiberizer can be a screenless, fixed hammer rotor type fiberizer available from Kamas Industries, a business having offices located in Sweden.

Upon exiting the fiberizer 30, the fiber streams 32 and 33 are operatively introduced into a directing channel 34 which delivers the fiber streams 32 and 33 from the fiberizer 30 to the forming chamber 40. The directing channel 34 can be any suitable conduit which is appropriately configured to allow an operative flow of the fiber streams 32 and 33 to the forming chamber. The directing channel can be of any operable, cross-sectional shape, and can be of any operable length. In the shown configuration, the directing channel 34 is substantially rectangular in cross-sectional shape and has its length aligned generally along the vertical direction. As a result, gravity can assist in the movement of the fiber streams 32 and 33 through the directing channel.

In particular aspects of the invention, the directing channel 34 can include a wall member 35 which laterally divides the directing channel 34 into a first channel section 36 and a second channel section 38. The separation wall member 35 helps to maintain the desired lateral separation between the fiber streams 32 and 33 during the transit from the fiberizer 30 to the forming chamber 40, and helps to provide laterally-coupled channel sections within the directing channel 34. Desirably the channel wall member 35 begins at a location which substantially, immediately adjacent to the outlet from the fiberizer 30, and extends to a location which is operatively adjacent to the appointed foraminous forming surface 48. As a result, each of the fiber streams 32 and 33 within the directing channel can be maintained with an individual composition which substantially corresponds to the composition of the material forming its associated fiber layer section 26 and 28, respectively.

The forming chamber 40 is connected to the end of the directing channel 34 and includes an upstream, front wall member 102, a relatively downstream, back wall member 104, and a pair of laterally opposed side wall members 106. The front wall member 102 provides an entrance opening 108 through which the moving forming surface 48 enters the forming chamber 40. The back wall member 104 includes an exit opening 110 through which the forming surface 48 and the formed fibrous web sections 76a and 76b exit from the forming chamber 40. The forming chamber 40 substantially encloses an operative section of the foraminous forming surface 48. During the transit of the enclosed portion of the forming surface 48 through the forming chamber 40, desired amounts of fiber material from the individual fiber streams 32 and 33 are deposited onto the forming surface to form the fibrous web sections 76a and 76b. Each of the fibrous web sections 76a and 76b can have an individual composition which substantially corresponds to its associated fiber stream 32 and 33, respectively. The movement of the airborne fibrous material in the fiber streams 32 and 33 onto the forming surface 48 has typically been referred to as an air-laying operation.

The illustrated configuration of the invention includes an internal chamber wall member 41 which operatively divides the forming chamber into a first chamber section 42 and a laterally adjacent second chamber section 44. The separation wall member 41 operatively maintains a desired lateral separation of the fiber streams 32 and 33 nearing the transit of the fiber streams through the forming chamber and onto the foraminous forming surface 48. The incorporation of a single chamber wall member 41 operatively provides a laterally-coupled forming chamber.

In the representatively shown configuration, the first and second chamber sections 42 and 44 are of substantially the same size. In particular, the first and second chamber sections have substantially equal cross-directional widths. Alternatively, the first and second chamber sections 42 and 44 may be of unequal size, and may be constructed with unequal cross-directional widths or other unequal dimensions, as desired to provide desired configurations for the formed fibrous web sections 76a and 76b.

The foraminous forming surface 48 can be provided by any operative technique, such as the surface of a forming belt, the peripheral surface of a rotatable forming drum, or the like, as well as combinations thereof. In the illustrated embodiment, for example, a forming drum 46 includes a peripheral, circumferentially and axially extending forming surface 48. The forming surface provides an appointed first surface section 50, and an appointed second surface section 52 which is positioned laterally adjacent to the first surface section. In particular aspects of the invention, the forming surface 48 can be operatively configured to provide desired shapes and thickness contours to the formed fibrous webs 76a and 76b. In particular, the first surface section 50 can be configured with a selected, first surface contour, and the second surface section 52 can be configured with a selected, second surface contour. The first surface section 50 can provide an appointed basis weight contour to the first fibrous web section 76a, and the second surface section 52 can provide an appointed second basis weight contour to the second fibrous web section 76b. Accordingly, the forming drum 46 can be configured to provide for a substantially simultaneous, laterally adjacent forming of selectively configured fibrous web sections 76a and 76b on the appointed forming surface 48, and the resultant web sections may be the same or different.

Figure 4:
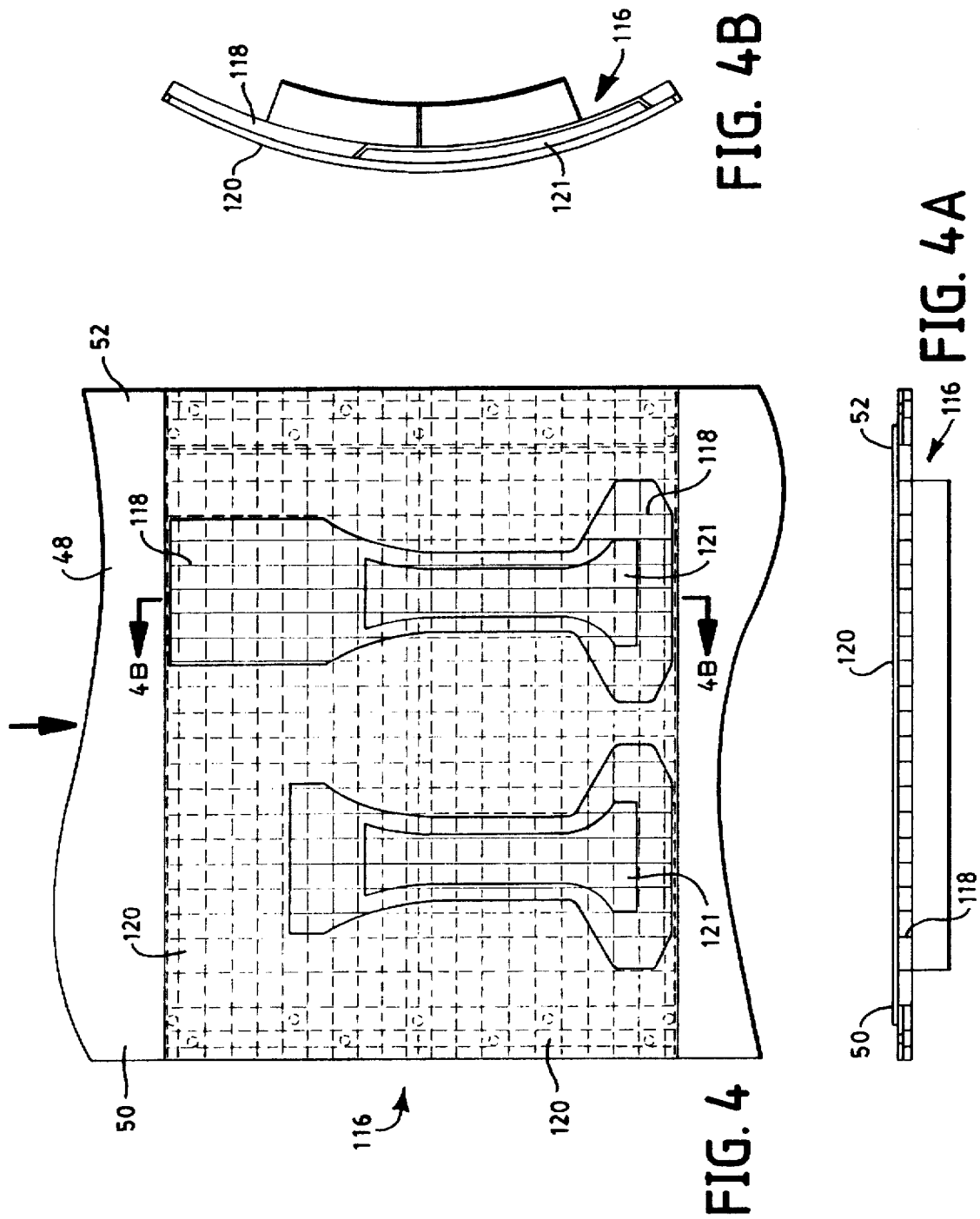
FIG. 4 representatively shows a schematic, top view of a segment of a foraminous forming surface employed with the invention.

With reference to FIGS. 4, 4A and 4B, the forming surface can be composed of a circumferentially extending series of repeating surface segments 116, which when combined together, provide for the forming surface 48 of the forming drum. In the representatively shown arrangement, each surface segment 116 includes a forming screen portion 118, and a masking layer 120 which is located adjacent to and radially outboard from the forming screen portion. The masking layer is configured to limit airflow at selected surface areas and to thereby help define desired side contours of the formed fibrous web sections. In addition, the outward surface of the forming screen portion 118 can be selectively contoured to provide a recessed pocket region 121 for producing an increased basis weight at appointed regions of the formed fibrous web sections 76a and/or 76b, as desired.

The forming drum includes a conventional vacuum system 54 to provide desired airflows through at least the portion of the forming surface 48 which is positioned within the forming chamber 40. The vacuum system draws an airflow through the forming surface into the forming drum, and each operating section of the forming surface has a portion of the vacuum system operatively constructed and arranged at a location which is radially inboard from its associated segment of the forming surface 48.

A conventional drum drive system 56 is operatively connected to rotate the forming drum in a desired speed and direction, and the shown arrangement of the forming drum is rotated in the clockwise direction. Various types of forming drum designs may be employed with the present invention. In particular, a suitable forming drum configuration is representatively shown in U.S. Pat. No. 4,666,647 entitled, APPARATUS AND PROCESS FOR FORMING A LAID FIBROUS WEB, issued May 19, 1987 to K. Enloe et al. (attorney docket No. 6900), the entirety of which is hereby incorporated by reference in a manner which is consistent herewith. In addition, various designs for the foraminous forming surface 48 can, for example, be found in U.S. Pat. No. 4,761,258 entitled, CONTROLLED FORMATION OF LIGHT AND HEAVY FLUFF ZONES, issued Aug. 2, 1988 to K. Enloe (attorney docket No. 6999), the entirety of which is hereby incorporated by reference in a manner which is consistent herewith.

With reference again to FIGS. 1 and 1A, the technique of the present invention can include a system for providing a layer of forming tissue or other porous woven or nonwoven fabric onto the foraminous forming surface 48. In the shown configuration, a layer of high-porosity tissue 79 is delivered from a tissue supply roll 78 for transport into the forming chamber 40, and is placed onto the forming surface of the forming drum 46 prior to the airlaying of the fiber streams 32 and 33. The tissue is sufficiently porous and air-permeable to allow the desired levels of airflow through its thickness needed for the airlaying operation. As a result, the fibrous web 76 can be formed onto the tissue layer 79. As the formed web 76 is removed from the forming drum surface, the tissue layer 79 is also removed to accompany the formed web 76 and to help maintain the integrity of the various portions of the formed web during the transport through subsequent processing operations. In particular aspects of the invention, the tissue layer 79 can help to provide desired performance characteristics, such as desired absorbency parameters, to the formed fibrous web 76.

Figure 7:
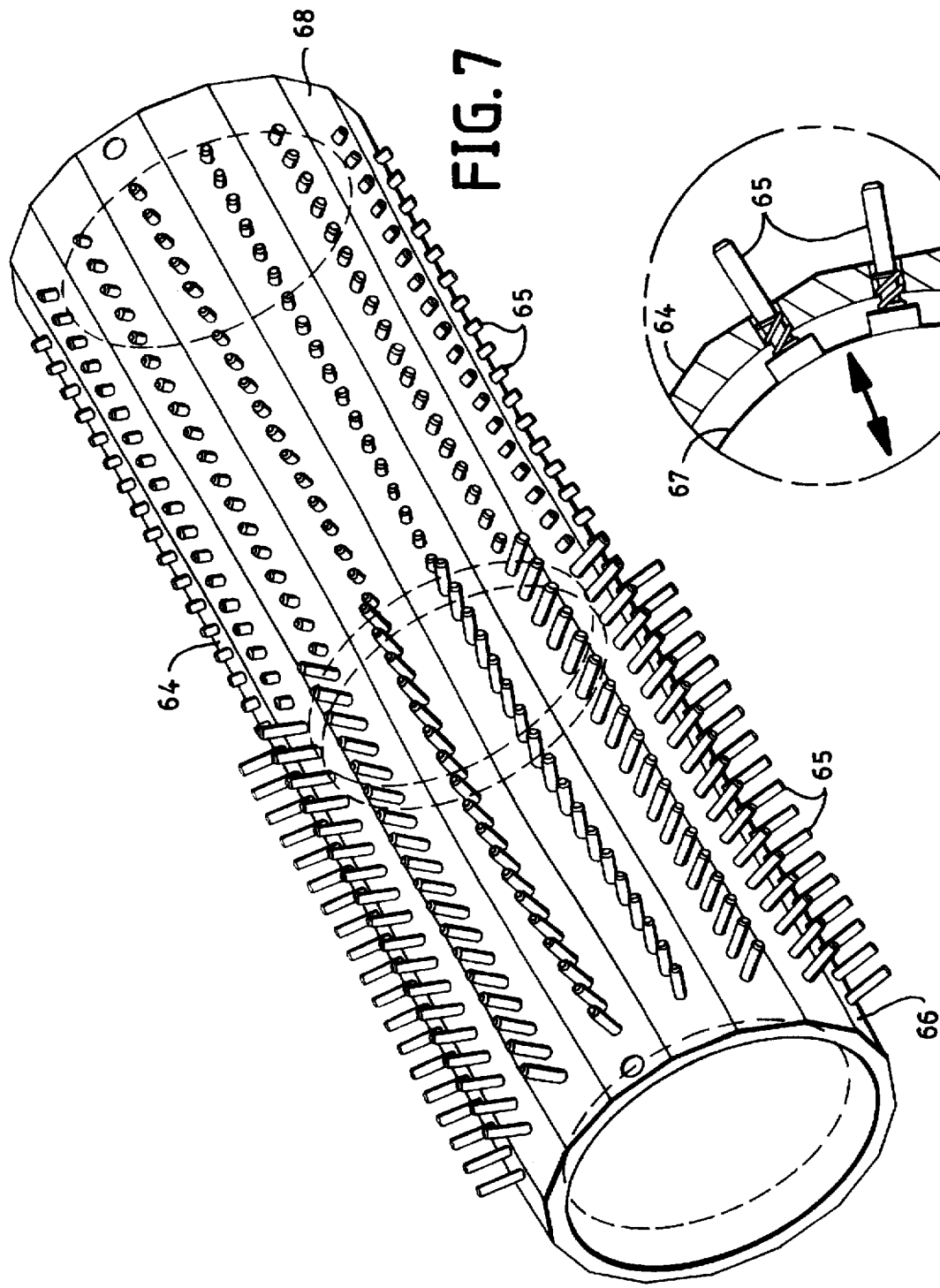
FIG. 7 representatively shows a schematic view of a multi-section scarfing roll which can be employed with the present invention.

After the fibrous web sections 76a and 76b have been airlaid and preliminarily formed, a rotatable scarfing roll 64 can be incorporated to abrade away or otherwise reduce a thickness or basis weight of at least one of the fibrous web sections 76a and 76b. As representatively shown, for example, the rotation of the forming drum can be arranged to move the fibrous web sections 76a and 76b out of the exit opening 110 of the forming chamber 40, and deliver the fibrous web sections to the scarfing roll system. In particular aspects of the invention, the scarfing roll 64 can include a first scarfing section 66 and a laterally adjacent second scarfing section 68, as representatively shown in FIGS. 2 and 7. Desirably, the second scarfing section is laterally coupled with the first scarfing section, and there is a substantially direct coupling between the scarfing sections. Optionally, there may be an indirect coupling between the scarfing sections, and the type of direct or indirect coupling may be mechanical, electromechanical, electromagnetic, electronic or the like, as well combinations thereof. The fibrous material removed from the appointed sections of the formed web 76 can be suitably collected for further processing. The representatively shown configuration, for example, employs a system of scarfing roll, take-away hoods 69 which operably collect the removed fibers for recycling into the fibrous web forming system.

The first and second scarfing sections 66 and 68 can be configured to provide substantially equal basis weights to each of the fibrous web sections 76a and 76b. In alternative aspects of the invention, the first and second scarfing sections can be configured to provide the first basis weight to the first fibrous web section 76a and a different, second basis weight to the second fibrous web section 76b, as representatively shown in FIGS. 7 and 7A. In particular aspects of the invention, the scarfing roll may include a mechanism for selectively adjusting the radial length of projection of the scarfing pins 65 above the outer peripheral surface of the scarfing roll 64 in at least one of the scarfing sections 66 and 68. For example the scarfing roll may include a selectively operable adjustment mechanism, such as the representatively shown internal air-bladder system 67, configured to selectively extend or retract the extension of the scarfing pins in the scarfing section 66 or 68. Accordingly, the effective scarfing diameter provided by one scarfing section can be controlled independently of the effective scarfing diameter provided by the other scarfing section.

Figure 2:
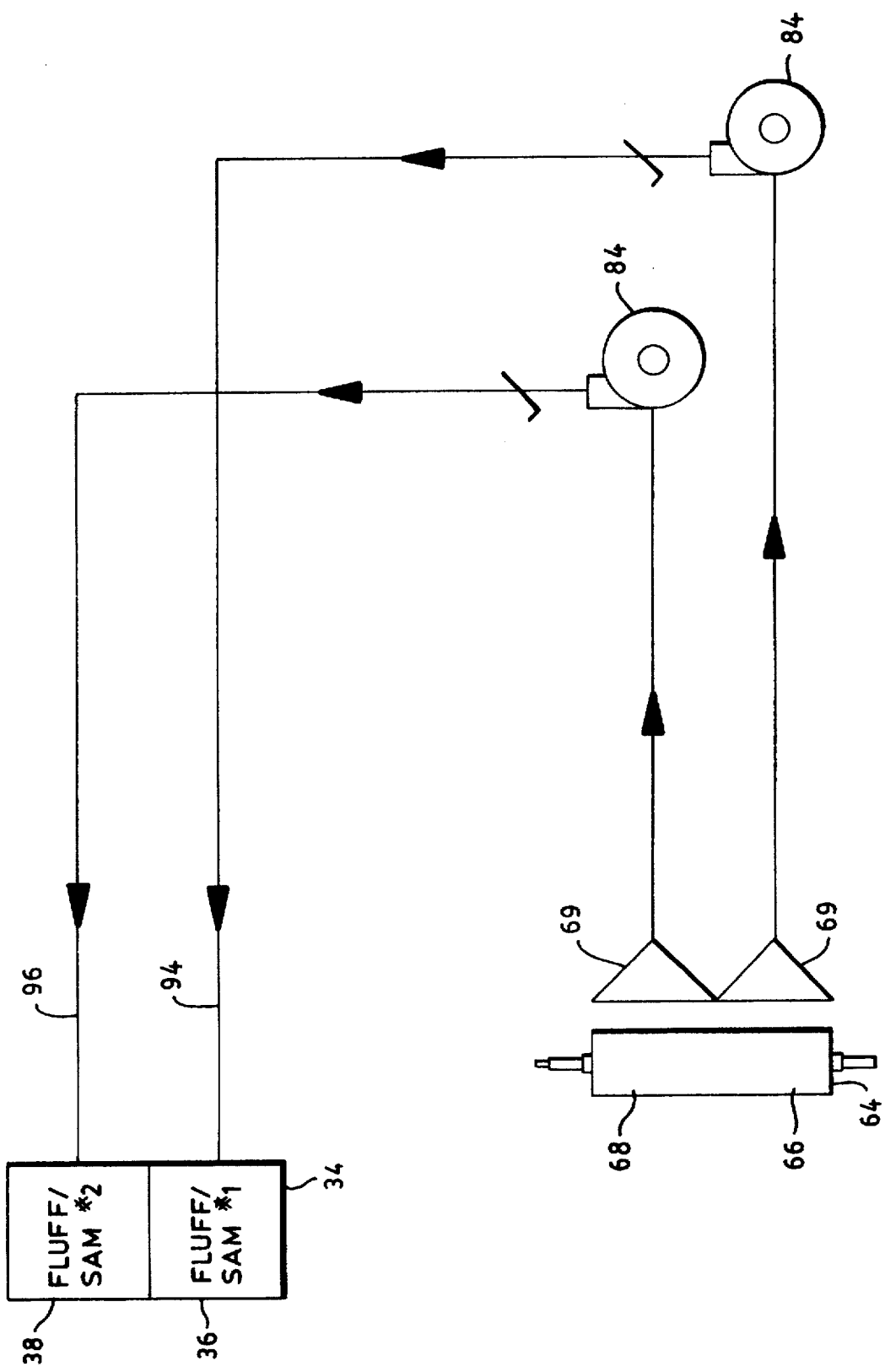
FIG. 2 representatively shows a schematic diagram of a fiber recycling system employed with the method and apparatus of the invention.

With reference to FIGS. 1 and 2, at least one recycling system can be employed to recirculate fibrous material which has been removed from the formed fibrous webs 76a and/or 76b by the various sections of the scarfing roll 64. The representatively shown configuration of the invention, for example, can include a first recycle duct 94 which is arranged in operative communication with the system of hoods 69 to receive fibrous material removed by the first scarfing roll section 66 and to direct and recirculate the removed fibrous material into the first directing channel section 36. Similarly, the invention can include a second recycle duct 96 which is arranged to receive removed fibrous material from the second scarfing roll section 68 and to direct and recirculate the removed fibrous material into a selected region of the second directing channel section 38. In addition, a suitable carrying mechanism, such as provided by the shown system of blower fans 84, drives and transports the removed fibrous material from the scarfing roll 64 back for reintroduction into the appropriate sections of the directing channel 34 and/or forming chamber 40.

A transporter, such as a mechanism which includes a take-off roll 60, operatively removes the fibrous web sections 76a and 76b from the forming surface 48. In addition, the forming drum can include a gas pressure, "blow-off" system to help separate the fibrous web sections from the forming surface. The transporter can also include a conveyor, such as provided by a system of belts or a system of rollers, which help to move the fibrous web sections 76a and 76b away from the forming drum 46. In particular aspects of the invention, the transporter can be configured to move the fibrous web sections in a side-by-side, laterally adjacent relation, and the fibrous web sections may or may not be directly attached to each other.

Figure 8:
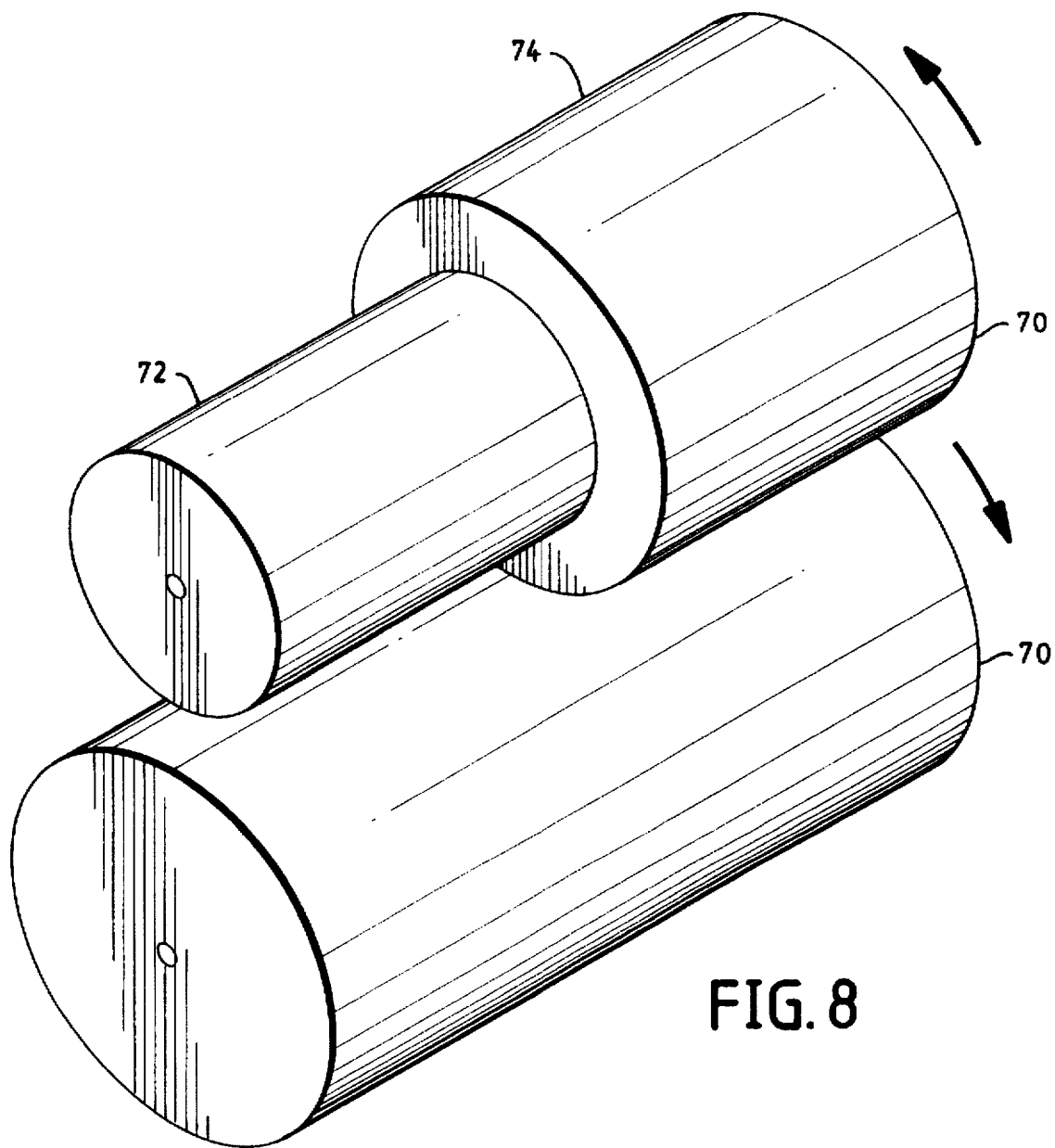
FIG. 8 representatively shows a schematic view of multi-section system of debulking rolls which can be employed with the present invention.

The method and apparatus of the invention can further include a system of rotatable compacting or debulker rolls 70 which operatively compress and increase the density of at least one, and desirably each, of the fibrous web sections 76a and 76b to a desired level. The shown arrangement includes at least one cooperating pair of counter-rotating rollers which compress the appointed web section in the nip region between the rollers. In particular aspects of the invention, the system of debulker rolls 70 can include a first debulker section 72 and a second debulker section 74. The first and second debulker sections can be configured to provide substantially equal densities to the formed fibrous web sections 76a and 76b. In alternative aspects of the invention, the first debulker section 72 can be configured to provide a first density to the first fibrous web section 76a, and the second debulker section 74 can be configured to provide a second, different density to the second fibrous web section 76b, as representatively shown in FIG. 8. In desired arrangements, the first and second debulker section 72 and 74 provide a pair of laterally-adjacent and laterally-coupled debulking sections, and there can be a substantially direct coupling between the debulking sections. Optionally, there may be an indirect coupling between the debulking sections, and the type of direct or indirect coupling may be mechanical, electromechanical, electro-magnetic, electronic or the like, as well as combinations thereof.

The selected transporter mechanism employed with the invention can then deliver the formed fibrous web sections 76a and 76b to an integrator 62 which laterally displaces at least a one of the fibrous web sections, such as the first fibrous web section 76a, and superposes the displaced fibrous web section onto another of the fibrous web sections, such as the second fibrous web section 76b, to provide the desired composite fibrous web 22.

Figure 5:
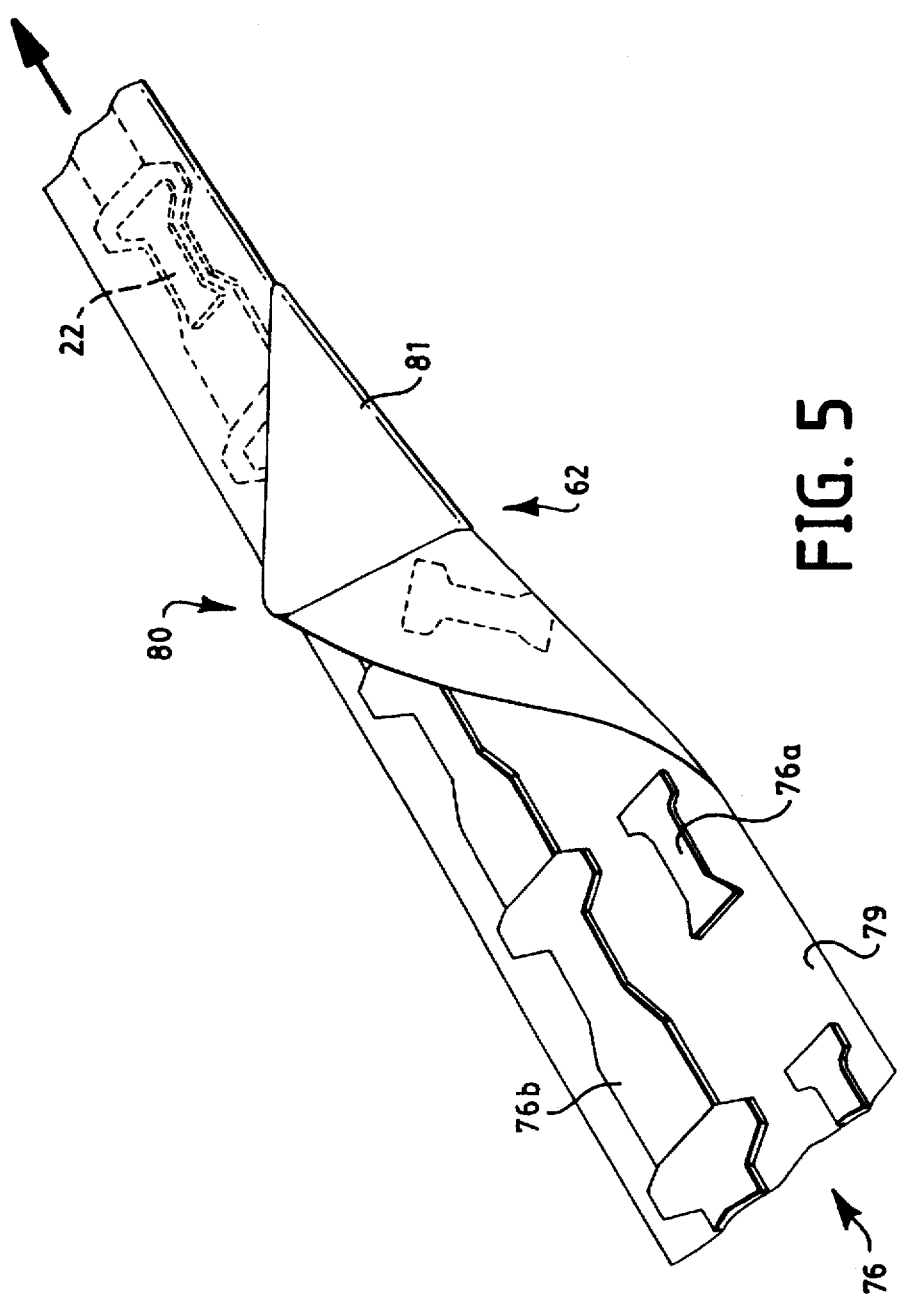
FIG. 5 representatively shows a formed fibrous web, and a folding technique employed with the present invention.

With reference to FIG. 5, the porous forming layer 79 can be configured to carry a formed fibrous web 76 having differently configured web sections. Desired aspects of the invention can be configured to provide an arrangement having a substantially continuously connected fibrous web portion, such as web section 76b, where there are substantially no gaps between the formed fibrous web segments. Alternatively, the invention can provide an arrangement having a substantially discontinuous fibrous web portion, such as web section 76a, where there are discrete gaps or spaced distances between the individual, formed fibrous web segments. The representatively shown configuration provides an further, optional combination having a substantially continuously connected web portion and a substantially discontinuous web portion.

Figure 9:
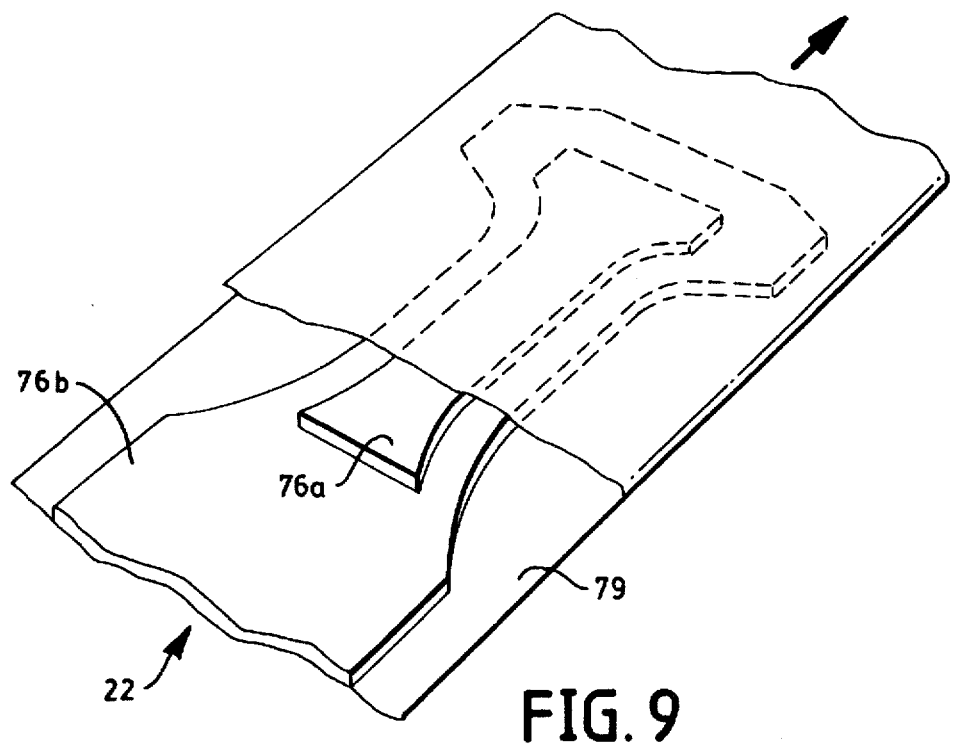
FIG. 9 representatively shows a schematic, partially cut-away view of a portion of a multi-layer, folded composite web which can be provided by the present invention.

In particular aspects of the invention, such as illustrated in FIG. 5, the integrator 62 can include a conventional folder mechanism 80. The folder mechanism can, for example, be provided for by a system of vacuum screen(s) and conventional folding mechanisms, such as the representatively shown folding board 81. The folder mechanism can pivot and rotate an appointed one of the formed web sections 76a or 76b about a selected folding line which extends longitudinally along the machine-direction of the web. The shown folding line, for example, is placed in between the first and second web sections 76a and 76b. Accordingly, the pivoted web section can then be placed in a superposed, face-to-face relation with the other web section in the resultant folding-type operation to provide the composite fibrous web 22, and a representative, partially cut-away section of the folded composite web 22 is illustrated in FIG. 9. In addition, an adhesive applicator may incorporated with the folding system to suitably apply a desired pattern of adhesive to hold the web sections together in a generally laminated configuration. Optionally, another conventional bonding mechanism may be employed to secure the composite web assembly.

Figure 6:
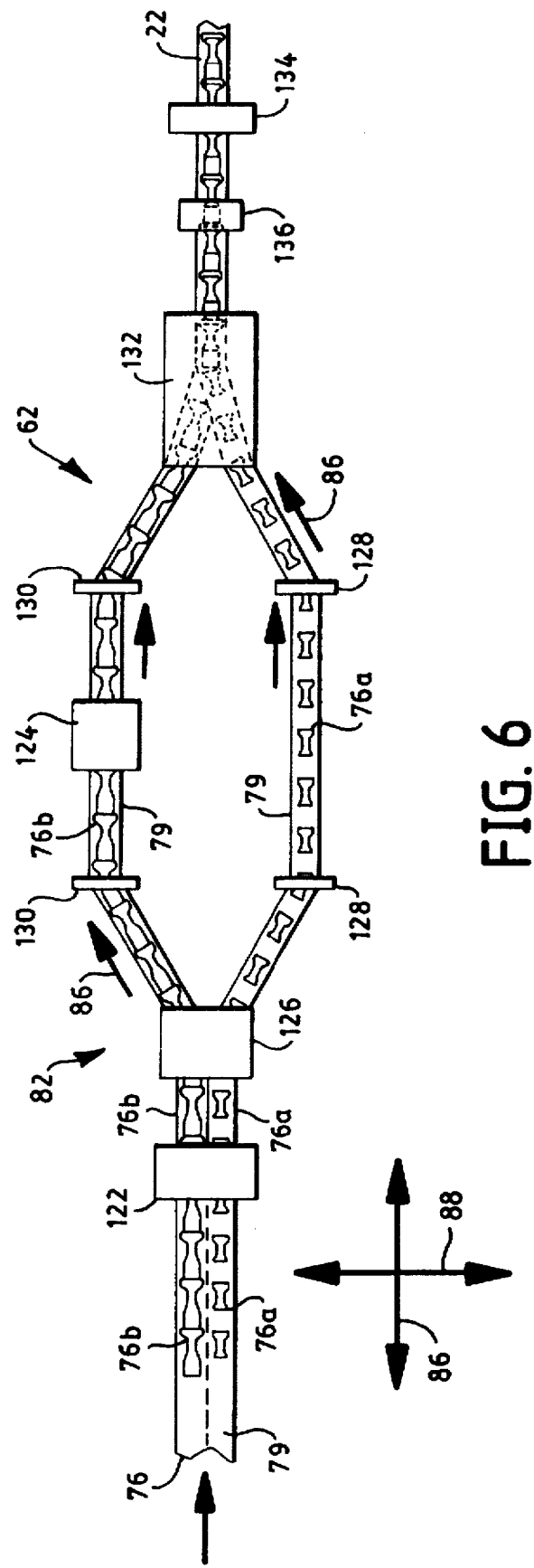
FIG. 6 representatively shows a technique for laterally displacing and positioning a first fibrous web section onto a second fibrous web section to form a configuration for a stacked composite web.

With reference to FIG. 6, the integrator 62 can alternatively include a translating mechanism 82 which operatively separates the first fibrous web section 76a from the second fibrous web sections 76b. The translating mechanism displaces the first fibrous web section relative to the second fibrous web section and positions the two fibrous web sections in an appointed superposed, stacked relationship. In particular aspects of the invention, the translating mechanism 82 can include a web dividing device such as a slitter 122, and web separator 126 which cooperate to space apart the formed web sections 76a and 76b. The web sections can then be suitably directed along desired paths by correspondingly associated systems of web guides 128 and 130, and an adhesive applicator system 124 may be employed to a distribute a selected distribution of assembly adhesive onto one of the web sections, such as the shown fibrous web section 76b. The guiding mechanisms can then operatively move the web sections 76a and 76b to a laminator 132 which merges the web sections into a stacked configuration to form a desired multi-layer fibrous web 22. Additionally, further assembly operations, such as provided by the alignment mechanism 136 and the shown pair of counter-rotating nip rollers 134 can be employed to complete a desired lamination of the fibrous web sections. The alignment mechanism helps to provide a desired registration and lateral placement of the first formed web section 76a relative to the second formed web section 76b. It should be readily appreciated that other components, such as vacuum screens, alignment devices and the like, as well as combinations thereof, may also be employed to further regulate and control the placement of one web section onto the other web section. It should also be readily appreciated that other attachment mechanisms may be employed to secure together the fibrous web sections 76a and 76b. Such attachment mechanisms can include mechanical bonding, thermal bonding, pressure bonding or the like, as well as operative combinations thereof. A representative, partially cut-away section of the stacked arrangement of the composite fibrous web 22 is illustrated in FIG. 10.

Figure 10:
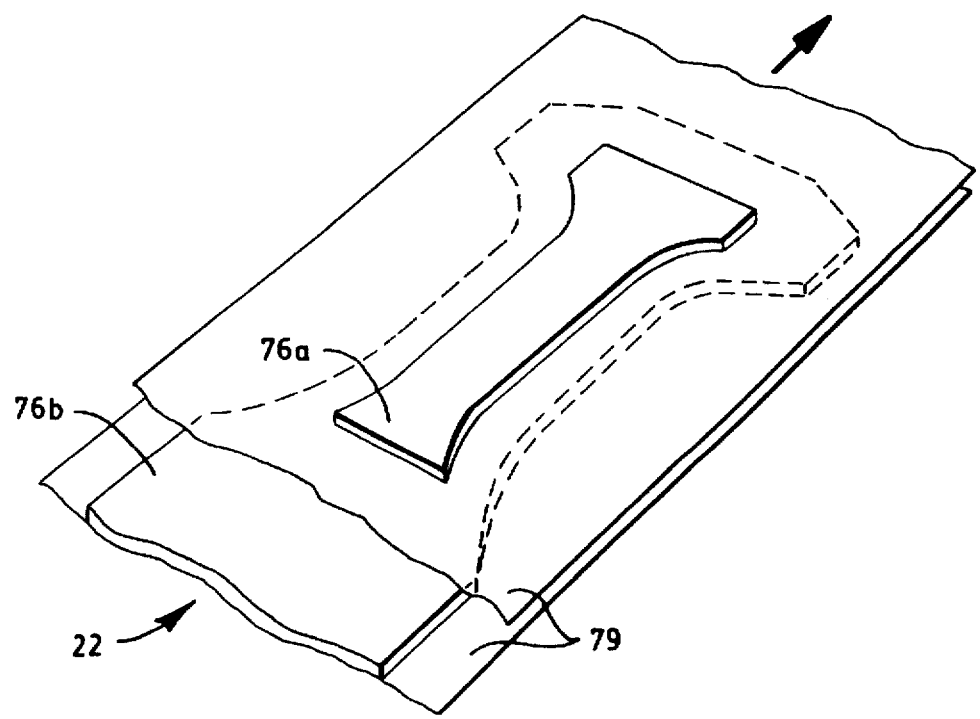
FIG. 10 representatively shows a schematic, partially cut-away view of a portion of a multi-layer, stacked composite web which can be provided by the present invention.

As representatively shown in FIGS. 9 and 10, the first fibrous web section 76a can be positioned in a substantially laterally-centered position on the second fibrous web section 76b. In alternative aspects of the invention, the first fibrous web section 76a may be located in a non-centered lateral position relative to the second fibrous web section 76b to provide desired performance characteristics.

Particular aspects of the invention can include a delivery passage which is configured to provide a selected particulate material into the process and apparatus. In particular aspects of the invention, the delivery passage or conduit is configured to deliver particles of superabsorbent material into at least one section of the directing channel 34. The illustrated arrangement, for example, has a first delivery conduit or passage 90 configured to provide a selected superabsorbent material into the first directing channel section 36, and has a second delivery conduit or passage 92 configured to provide a selected superabsorbent material into the second directing channel section 38. In particular arrangements, substantially the same type of superabsorbent material may be supplied by the delivery conduits 90 and 92. In alternative aspects of the invention, the first delivery conduit 90 may provide a first type of superabsorbent material, and the second delivery conduit 92 may supply a second, different type of superabsorbent material. The various types of superabsorbent material may differ with respect to any desired absorbency or physical characteristic, such as particle size, particle shape, amount, absorbent capacity, absorbency rate, absorbency under load characteristics, gel strength, or the like.

The delivery conduit 90 or 92 for each supply stream of superabsorbent material can also include a regulating mechanism for controlling the volume rate or mass rate of delivery of each type of superabsorbent material through its associated delivery conduit 90 or 92. The illustrated embodiment, for example, includes a first superabsorbent feed regulator 112 operatively connected to the first delivery conduit 90, and a second superabsorbent material feed regulator 114 operatively connected to the second delivery conduit 92. Various types of conventional regulating mechanisms may be employed for the superabsorbent feed regulator 112 and 114. For example, metering devices, such as a K-TRON weight and loss feeder, Model number K10S, can be employed as a suitable feed rate regulator with the present invention.

It should be readily apparent that the various characteristics and structural parameters of the individual formed fibrous web sections 76a and 76b can be adjusted and modified by appropriately adjusting the movement speeds and input rates of the various components. For example, the basis weight can be modified by adjusting the feed rate of the fiber layer sections 26 and 28 into the fiberizer, and the fiber-to-superabsorbent ratio can be adjusted by regulating the superabsorbent feed rates into the fiber streams 32 and 33. The density and/or thickness can be adjusted by modifying the configuration and operation of the scarfing roll, and the densities can be regulated by adjusting the configuration and operation of the debulker rolls 70.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An apparatus for forming a composite fibrous web, comprising:

a web supply which provides at least two appointed fiber layer sections of fiber material, each of said layer sections having a selected composition;

a fiberizer which disintegrates each of said fiber layer sections into individual, laterally adjacent fiber streams having said selected compositions, said fiberizer configured to disintegrate said fiber layer sections while substantially maintaining a lateral separation of said fiber streams while moving said fiber streams through said fiberizer;

a directing channel which delivers said fiber streams from said fiberizer to a forming chamber, said forming chamber configured to substantially maintain said separation of said fiber streams;

a movable foraminous forming surface disposed within said forming chamber, said forming surface configured to receive each of said fiber streams to produce individual, fibrous web sections substantially corresponding to said individual fiber streams;

a transporter which removes said fibrous web sections from said forming surface; and an integrator which laterally displaces at least a one of said fibrous web sections to superpose said one of said fibrous web sections onto another of said fibrous web sections to provide said composite fibrous web.

2. An apparatus as recited in claim 1, wherein said foraminous forming surface is provided by a peripheral surface of a rotatable forming drum.

3. An apparatus as recited in claim 1, wherein said foraminous forming surface is disposed within a forming chamber having laterally-coupled chamber sections, and said directing channel is configured to substantially maintain said separation of said fiber streams.

4. An apparatus as recited in claim 1, further comprising a rotatable scarfing roll for reducing a thickness of at least one of said fibrous web sections.

5. An apparatus as recited in claim 1, further comprising a rotatable debulker roll for compacting at least one of said fibrous web sections.

6. An apparatus as recited in claim 1, wherein said at least two fiber layer sections have different compositions.

7. An apparatus as recited in claim 1, wherein said fiberizer is configured to provide not more than about 10% lateral mixing between the fiber streams, as determined with respect to a total basis weight of an individual fibrous web section.

8. An apparatus as recited in claim 1, wherein said web supply is configured to provide said fiber layer sections in a substantially side-by-side, laterally adjacent relation.

9. An apparatus as recited in claim 1, wherein said fiberizer is configured to provide each of said fiber streams with only a single pass of each said fiber layer sections of fiber material through said fiberizer.

10. An apparatus as recited in claim 1, wherein said foraminous forming surface is configured to provide for a substantially simultaneous, lateral forming of said fibrous web sections.

11. An apparatus as recited in claim 1, wherein said fiberizer is configured with substantially no internal baffling arranged to maintain said lateral separation of said fiber streams while said fiber streams are moving through said fiberizer.

12. An apparatus as recited in claim 1, wherein said integrator is configured to provide a folding movement to laterally displace said at least one fibrous web section, and to superpose said one of said fibrous web sections onto said other of said fibrous web sections.

13. An apparatus as recited in claim 1, wherein said fiberizer has fiberizer sections configured to simultaneously disintegrate said fiber layer sections.

14. An apparatus as recited in claim 1, wherein said fiberizer is configured with fiberizer sections which are laterally-coupled with a direct, mechanical coupling.

15. An apparatus as recited in claim 1, further comprising a delivery passage which is configured to provide a selected superabsorbent material into at least one section of said directing channel.

16. An apparatus as recited in claim 15, wherein a first delivery passage is configured to provide a selected superabsorbent material into a first directing channel, and a second delivery passage is configured to provide a selected superabsorbent material into a second section of said directing channel.

17. An apparatus as recited in claim 16, wherein said first delivery passage is configured to provide a first superabsorbent material into said first directing channel, and said second delivery passage is configured to provide a second, different superabsorbent material into said second directing channel.

18. An apparatus as recited in claim 1, wherein said web supply is configured to provide a first fiber layer section at a first input rate, and provide a second fiber layer section at a different, second input rate.

19. A method for forming a composite fibrous web, comprising a lateral displacing of at least one fibrous web section to superpose a first fibrous web section onto a second fibrous web section to form a composite fibrous web; said first and second fibrous web sections having been provided by a supplying of at least two appointed, fiber layer sections of fiber material, each of said layer sections having a selected composition;

a disintegration of each of said fiber layer sections into individual, laterally adjacent fiber streams having said selected compositions, said disintegration of said fiber layer sections conducted while substantially maintaining a lateral separation of said fiber streams while moving said fiber streams through said disintegration operation;

a delivering of said fiber streams to a forming chamber which substantially maintains said lateral separation of said fiber streams;

a receiving of said fiber streams onto a foraminous forming surface within said forming chamber to produce individual, fibrous web sections substantially corresponding to said individual fiber streams; and a removing of said fibrous web sections from said forming surface.

20. A method as recited in claim 19, wherein said directing channel has been configured to substantially maintain said lateral separation of said fiber streams.

21. A method as recited in claim 19, wherein a basis weight of at least one of said fibrous web sections has been reduced with a rotatable scarfing roll, and at least one of said fibrous web sections has been compacted with a rotatable debulker roll.

22. A method as recited in claim 19, wherein said first fibrous web section has been supplied with a first fiber composition, and said second fibrous web section has been supplied with a different, second fiber composition.

* * * * *